US008265366B2

United States Patent
Dow et al.

(10) Patent No.: US 8,265,366 B2
(45) Date of Patent: Sep. 11, 2012

(54) GENERATION OF STANDARD PROTOCOLS FOR REVIEW OF 3D ULTRASOUND IMAGE DATA

(75) Inventors: Alisdair Dow, Snohomish, WA (US); James Jago, Seattle, WA (US); Antoine Collet-Billon, Paris (FR); Lisa Pumphrey, Kenmore, WA (US)

(73) Assignee: Koninklijke Philips Electronic N.V., Eindhoven (NL)

( * ) Notice: Subject to any disclaimer, the term of this patent is extended or adjusted under 35 U.S.C. 154(b) by 0 days.

(21) Appl. No.: 13/119,636

(22) PCT Filed: Sep. 11, 2009

(86) PCT No.: PCT/IB2009/053986
§ 371 (c)(1),
(2), (4) Date: Mar. 17, 2011

(87) PCT Pub. No.: WO2010/035167
PCT Pub. Date: Apr. 1, 2010

(65) Prior Publication Data
US 2011/0172536 A1 Jul. 14, 2011

Related U.S. Application Data

(60) Provisional application No. 61/099,612, filed on Sep. 24, 2008.

(51) Int. Cl.
*G06K 9/00* (2006.01)
(52) U.S. Cl. ............ 382/128; 324/754.25; 324/500
(58) Field of Classification Search .............. None
See application file for complete search history.

(56) References Cited

U.S. PATENT DOCUMENTS

| | | | |
|---|---|---|---|
| 2005/0054927 A1* | 3/2005 | Love | 600/443 |
| 2008/0319316 A1* | 12/2008 | Powers et al. | 600/439 |
| 2011/0201934 A1* | 8/2011 | Robinson | 600/443 |

FOREIGN PATENT DOCUMENTS
EP 0997851 A2 5/2000
* cited by examiner

*Primary Examiner* — Melissa Koval
*Assistant Examiner* — Trung Nguyen
(74) *Attorney, Agent, or Firm* — W. Brinton Yorks, Jr.

(57) ABSTRACT

An ultrasonic diagnostic imaging system is described which records expert review of a 3D image data set, including image plane and view manipulation, annotation, and measurements, for the purpose of generating automated review protocols for 3D ultrasound image acquisitions. The ability to provide a standardized 3D review protocol has benefits such as guiding reviewers of all experience levels through the required steps to extract key images and measurements from 3D image data, enabling automation to improve 3D review workflow and reduce review time, monitoring growth or therapy, and standardizing review presentations for easy comparison with prior examination results.

11 Claims, 8 Drawing Sheets

GENERATION OF STANDARD PROTOCOLS FOR REVIEW OF 3D ULTRASOUND IMAGE DATA

This invention relates to medical diagnostic ultrasound systems and, in particular, to ultrasound systems which enable efficient review and diagnosis using three dimensional (3D) ultrasound image data.

As ultrasound diagnosis has become more sophisticated and the technology more refined, ultrasound imaging systems have become more specialized and configured for imaging specific anatomy during certain specific types of examinations such as obstetrics, cardiology, vascular and radiology. With this specialization of ultrasound the practice of ultrasound diagnosis has become more standardized, with specific image acquisition protocols being designed for acquiring images of patients with specific symptoms or characteristics. For example, a general abdominal exam protocol may call for the acquisition of particular views of the liver, kidneys, gall bladder and pancreas. A general vascular exam may call for the acquisition of particular views of the carotid artery and vasculature of the limbs of the body. Ultrasound imaging system manufacturers have followed this trend by providing their systems with pre-programmed exam protocols to guide the sonographer through the gathering of these specific image sequences. These pre-programmed exam protocols also enable ultrasound imaging systems to produce reports automatically tailored to the specified information. Such pre-programmed protocols and reporting have improved the efficiency of conducting ultrasound exams.

Pre-programmed protocols, particularly those for a general survey exam, are generally designed to step the sonographer through a series of views, measurements, and calculations in particular regions of the body to determine whether the imaged anatomy is normal or exhibits suspect characteristics. In addition to these pre-programmed protocols, more sophisticated ultrasound imaging systems typically allow the sonographer to design custom protocols, which include custom ultrasound image acquisition ordering, system setup, measurements and calculations not provided by a default protocol in the ultrasound imaging system. This valuable feature frees the sonographer from the restriction of using only the protocols provided with the ultrasound imaging system and variations thereof, and enables sonographers and researchers to develop their own new and more efficient protocols and system configurations.

There are many clinical applications in which it is more beneficial to obtain ultrasound volume images rather than conventional two dimensional (2D) images. Examples include clinical applications where multiple key images are desired from a single organ, where out of plane information provides important context to the review of acquired data, or where key images are difficult to obtain in 2D due to orientation relative to acoustic windows. In these cases 3D offers the potential to reduce the number of acquisitions required. This is because an entire organ or tissue being diagnosed can be centered in the viewing region of a 3D probe end, with a click of the "capture" button, a volume of the entire anatomy being diagnosed can be acquired. Diagnosis of a volume image can be problematic, however. That is because anatomical landmarks can be obscured by surrounding tissue, blood vessels can be intertwined and follow tortuous paths, and the anatomy may take on an unusual or unexpected shape. But principally the difficulty in diagnosing 3D volume images resides in the fact that sonographers and physicians are accustomed to making diagnoses from planar 2D ultrasound images, not 3D volume images. Accordingly, most 3D ultrasound image viewers have the ability to view different planes of a 3D volume. One common approach is to show the user three orthogonal intersecting "cut planes" through the volume. The user is given the ability to change the locations of the cut planes in the volume. By changing the x,y,z coordinates of the three planes, the clinician can obtain the planar images familiar to him or her for the necessary diagnosis. Thus, the diagnostic challenge has changed from acquiring the necessary 2D images to navigating through the volume image to find the image planes desired for diagnosis. The challenge in 3D ultrasound imaging is to be able to consistently navigate through the volume to all of the images that are important for patient assessment.

Numerous efforts and image processing techniques have been developed to assist the clinician in navigating through a volumetric ultrasound image. One approach is to provide automated image analysis which is designed to automatically find image planes with predetermined anatomical landmarks. These image planes from volumetric image data are referred to as "standard views." One approach to finding standard views is described for instance in international patent publication no. WO 2006/105071. Image analysis approaches can be thwarted, however, by the different ways in which anatomical landmarks and standard views can appear in the anatomy of different individuals. Another approach is a technique for generating statistics from manually determined spatial relationships between specific planar images as described in US patent publication nos. 2005/0004465 and 2005/0251036. Such approaches can be tedious and can also encounter anatomy with high statistical variation. Within 3D ultrasound imaging one of the most difficult tasks remains the user navigation from one location of interest in the volume to another. Thus it is desirable to provide a clinician with the ability to rapidly and confidently navigate through a volumetric ultrasound image to find the image planes needed for diagnosis. Preferably this capability should be in the form of a diagnostic protocol designed to enable the clinician to quickly acquire the necessary 3D volume data and navigate to the desired planar images.

In accordance with the principles of the present invention, a diagnostic ultrasound system and method are described which enable the recording of expert review of a 3D ultrasound image data set, including 3D manipulation, annotation, measurements and capture of images, for the purpose of generating standard review protocols for 3D ultrasound acquisitions. The recorded manipulations of 3D data can be replayed to navigate through other 3D volumes, particularly in the case of serial studies of the same patient. This capability can guide reviewers of all experience levels through the required steps to extract key images and measurements from 3D data, enabling automation to improve 3D review workflow and reduce review time, and the monitoring of growth or therapy of target anatomy for easy comparison with prior image data. The record feature can also be used to generate statistics for determining relationships between anatomical features.

Figure 1:
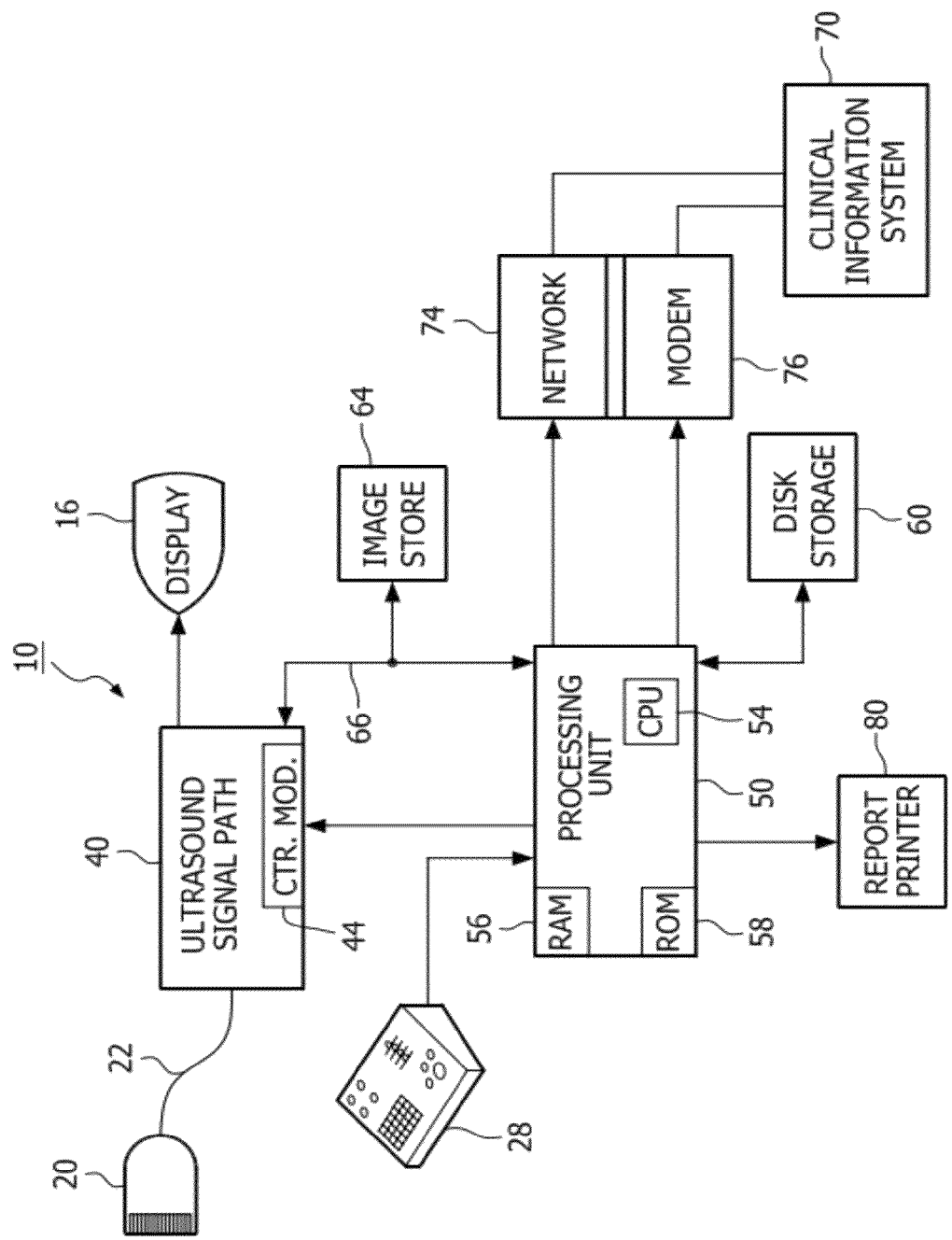
FIG. 1 illustrates in block diagram form an ultrasonic diagnostic imaging system constructed in accordance with the principles of the present invention.

Referring first to FIG. 1, an ultrasound system 10 constructed in accordance with the principles of the present invention is shown in block diagram form. A 3D ultrasound imaging probe 20 is coupled by the cable 22 to an ultrasound signal path 40 which processes 3D ultrasonic image data. The ultrasound signal path 40 includes a transmitter coupling electrical signals to the probe 20, an acquisition unit that receives electrical signals from the probe 20 corresponding to ultrasound echoes, a signal processing unit that processes the signals from the acquisition unit to perform a variety of functions such as isolating returns from specific depths or isolating returns from blood flowing through vessels, and a scan converter that converts the signals from the signal processing unit so that they are suitable for use by the display 16. The processing unit in this example is capable of processing both B mode (structural) and Doppler (motion) signals for the production of various 3D B mode and Doppler images, including spectral Doppler images. The ultrasound signal path 40 also includes a control module 44 that interfaces with a processing unit 50 to control the operation of the above-described units. The ultrasound signal path 40 may, of course, contain components in addition to those described above, and, in suitable instances, some of the components described above may be omitted.

The processing unit 50 contains a number of components, including a central processor unit ("CPU") 54, random access memory ("RAM") 56, and read only memory ("ROM") 58, to name a few. As is well-known in the art, the ROM 58 stores a program of instructions that are executed by the CPU 54, as well as initialization data for use by the CPU 54. The RAM 56 provides temporary storage of data and instructions for use by the CPU 54 and may also store programs which are executed by the CPU. The processing unit 50 interfaces with a mass storage device such as a disk storage drive 60 for nonvolatile storage of data, such as data corresponding to ultrasound images obtained by the system 10. However, such image data is initially stored in an image storage device 64 that is coupled to a signal path 66 extending between the ultrasound signal path 40 and the processing unit 50. The disk drive 60 also preferably stores protocols which may be called up and initiated to guide the sonographer through various ultrasound exams.

The processing unit 50 also interfaces with a keyboard and controls 28. The keyboard and controls 28 may also be manipulated by the sonographer to cause the ultrasound imaging system 10 to produce automatically generated reports at the conclusion of an examination. The processing unit 50 preferably interfaces with a report printer 80 that prints reports containing text and one or more images. The type of reports provided by the printer 80 depends on the type of ultrasound examination that was conducted by the execution of a specific protocol. Data corresponding to images may be downloaded through a suitable data link, such as a network 74 or a modem 76, to a clinical information system 70 or other device.

Figure 2A:
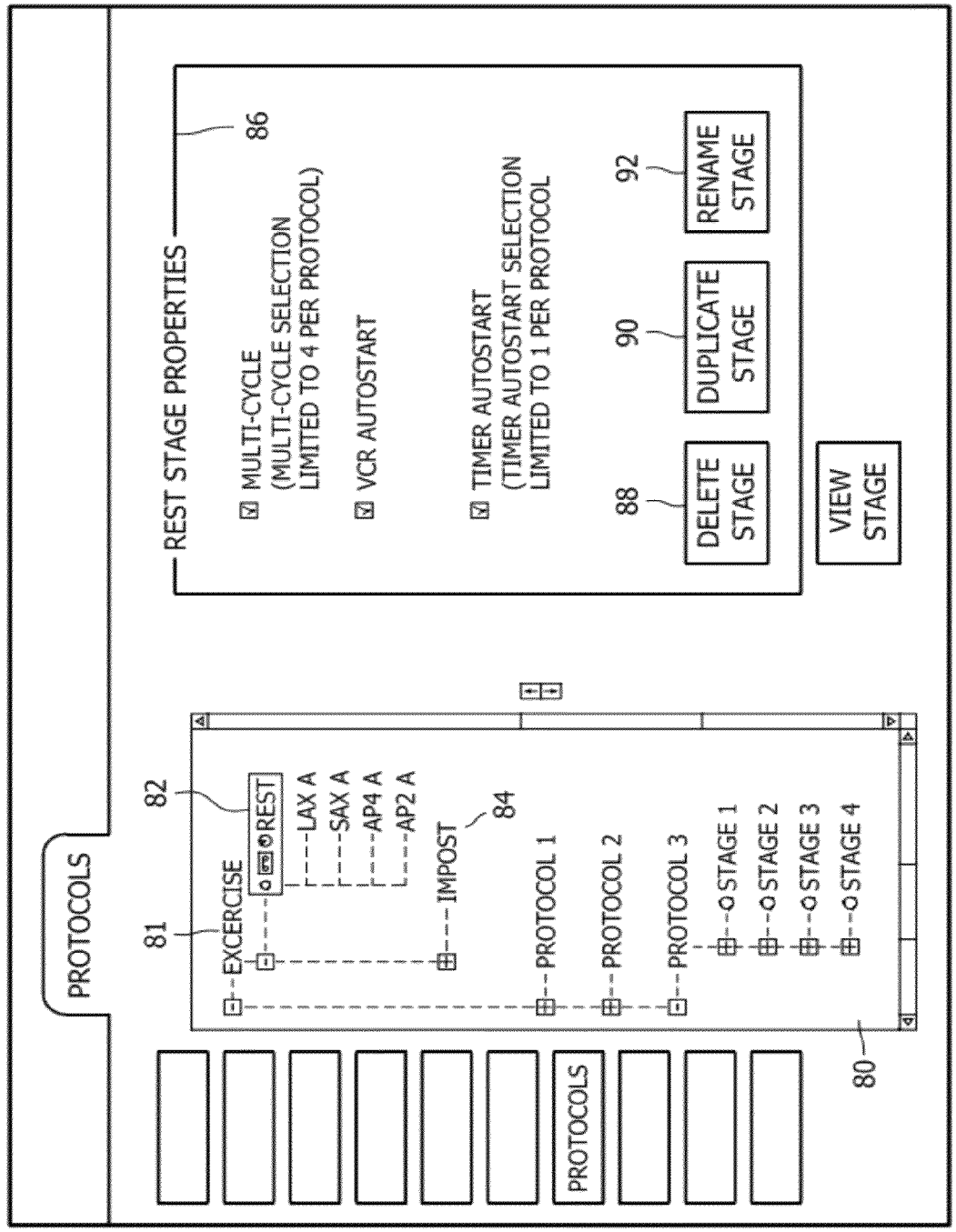
FIGS. 2a and 2b illustrate examples of an ultrasound system user interface used in conjunction with managing and using ultrasound imaging protocols.
Figure 2B:
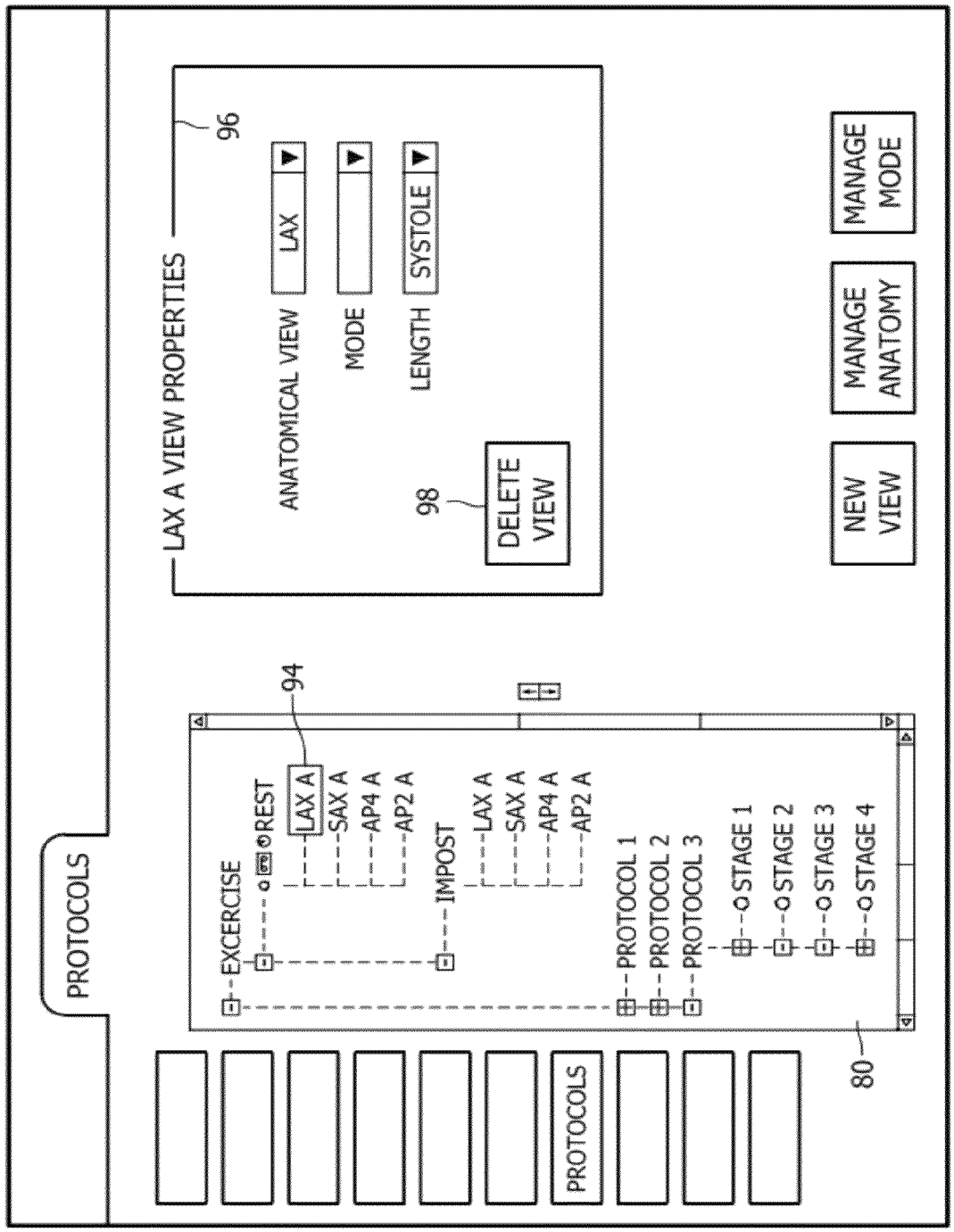

A typical user interface for managing ultrasound imaging protocols is illustrated in FIGS. 2a and 2b. The left side of both FIGS. 2a and 2b illustrates a protocol tree 80. The protocol tree 80 shows a hierarchical structural rendering of a typical cardiac examination protocol. Such an examination consists of two stages. One stage comprises acquiring ultrasound images and measurements during a pre-exercise or resting state, whereas the second stage usually consists of acquiring the same ultrasound images and measurements immediately post-exercise. As will be understood by one of ordinary skill in the art, these stages are generally referred to as the 'rest' and 'impost' stages respectively. A protocol stage consists of all the images and measurements acquired during that stage. Each image or measurement is generally called a 'view.'

With reference to FIG. 2a, the exercise protocol 81 consists of two stages: stage Rest 82 and stage Impost 84. Stage Rest 82 has been selected and expanded within the hierarchical tree and all of the views of this stage are visible. The views are represented by the textual labels "LAX A," "SAX A," "AP4," and "AP2." Such labels denote long-axis, short-axis, apical four-chamber and apical two-chamber image views as will be understood by those of ordinary skill in the art. Because stage Rest 82 is selected, the right side of FIG. 2a shows the stage properties dialog 86 that displays the properties of the selected stage and provides the sonographer with buttons for performing management operations on the stage. More specifically, the "Delete Stage" button 88, "Duplicate Stage" button 90 and "Rename Stage" button 92 allow the sonographer to delete, copy and rename the stage.

FIG. 2b differs from FIG. 2a in that the LAX A view 94 is selected instead of stage Rest 82. The left side of FIG. 2b displays the protocol tree 80 whereas the right side shows the view properties box 96 because the LAX A view 94 is selected. In addition to displaying the properties of the LAX A view 94, the view properties box 96 provides the sonographer with the ability to delete the selected view by pressing the "Delete view" button 98. By use of the buttons shown in these drawings the user of the ultrasound system can add, delete, and edit the different stages and views of a protocol which is stored on the system. A user can also create entirely new protocols for new diagnostic procedures. Once a protocol has been defined it can be recalled and run, guiding a sonographer through the acquisition of ultrasound images needed to make a specific diagnosis. The protocol will usually automate much of the acquisition such as by automatically setting up the operating parameters of the ultrasound system needed to acquire a certain image or image sequence. In the example of FIGS. 2a and 2, the illustrated protocol guides the sonographer through the images to be acquired during a stress echo exam including the initial resting phase, stage Rest 82, and the subsequent exercise phase, stage Impost 84. After the images are acquired they are generally forwarded in the form of a stress echo report to a cardiologist, who will read the images and make the appropriate diagnosis of the cardiac performance of the patient.

In accordance with the principles of the present invention, these concepts of standardization and automation of an acquisition protocol are extended to the post-acquisition diagnostic phase of patient care. In effect, the present invention describes a "review protocol" by which a physician is assisted in navigating through a previously acquired 3D volumetric image to find the planar images from which a diagnosis can be made. This review of 3D data may be made by an expert whose manipulations are recorded and replayed to navigate through subsequently acquired 3D image data sets of the same anatomy of the same or a different patient. A particularly suitable application of the present invention is to record the navigation of a clinician through a first 3D data set of a patient, then replay the recorded manipulations to navigate through a 3D image data set subsequently acquired of the same patient's anatomy in a serial study. In addition to automatically navigating through the 3D image data, a review protocol of the present invention can also perform familiar protocol actions such as setting up imaging parameters and annotations, automatically launching measurement tools, and stepping the user from one standard or reference planar image to the next. In such an embodiment acquisition and review can both be automated in the same protocol.

For example, an operator may need to navigate to, and evaluate, many planes within a 3D volume of data and measure and/or annotate them accordingly, just as they would perform similar actions during a real-time exam with 2D images. As a user navigates through a volume, each of the manipulations are recorded, including but not limited to the translation of the center of interest to an anatomical location, rotation of an MPR (multi-planar reconstructed) view around a given axis by a specific angle, translation of the MPR view by a certain distance. The protocol also records presentation information such as annotations that the user enters, identifying the images captured, the imaging settings, and the display layout that is chosen for capture. Both during and after completing the review of the exam the user can edit the steps and add instructions to guide users or an automated system from one step to the next. For example an instruction can be entered to "Translate the center of interest in MPR A from the Crux to the Aorta". The protocol can also record the specific relationships between the images for use in statistics generation or for replicating the image capture in a follow up exam on the same patient.

Figure 3:
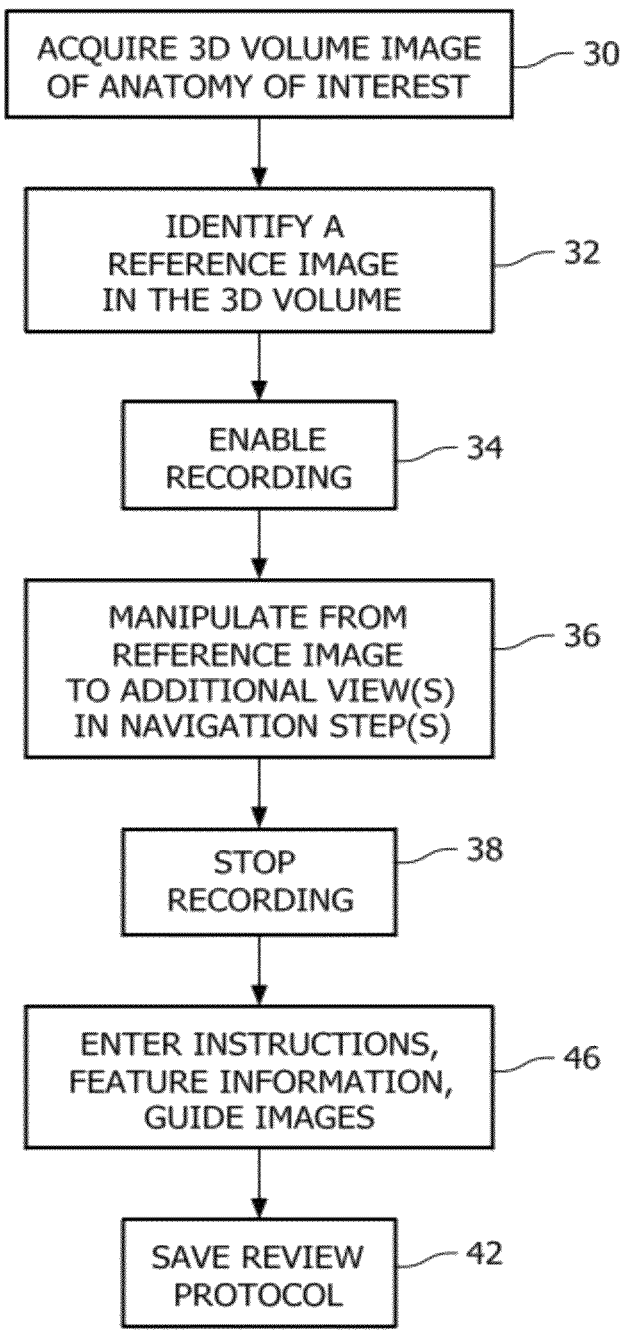
FIG. 3 is a flowchart of a sequence of steps for developing an automated 3D image data review process of the present invention.

FIG. 3 is a flowchart of steps for developing a 3D review protocol of the present invention. In step 30 the clinician acquires a 3D volume image of the anatomy of interest. If the anatomy of interest were the heart, for example, the 3D volume could include the patient's heart. If the anatomy of interest were the fetal cranium, the 3D volume of interest would include the head of the fetus, for instance. In step 32 the clinician identifies a reference image in the 3D volume image. This step presumes that the clinician is using a 3D viewer which displays one or more cut planes through the volume of image data. Preferably the 3D viewer simultaneously displays three orthogonal cut planes through the volume. Such cut planes are referred to as multi-planar reconstructed (MPR) image planes, because the planar images are reconstructed from addressed planes of the 3D volume data. For example, the voxels of a volume of 3D image data can be addressed in x, y, and z coordinates. An image plane can be reconstructed by displaying all x and y voxels with the same z coordinate. By changing the z coordinate, other parallel planes can be reconstructed and displayed. An orthogonal image plane can be reconstructed by displaying all y and z voxels with the same x coordinate, for example. In step 32 the clinician adjusts the MPR coordinates to display a reference image, a 2D image with identifiable landmarks in it. For example, a reference heart image may be an image through the mitral valve plane. A reference fetal image may be an image through the center of the fetal spine. The selection of a reference image is preferably done with graphic tools which enable the clinician to select a plane by dragging on or through an image or graphical markers which can be moved such as the location line of one plane in relation to another or in relation to the volume. The reference image provides a known starting point from which the subsequent 3D image manipulations proceed.

In step 34 the clinician enables the recording of the following manipulations and other related information such as display settings and layout. In step 36 the clinician begins to manipulate the 3D image data starting from the display of the reference image. These manipulations are designed to proceed from the known starting point to a desired endpoint where a 2D image that is useful for the intended diagnosis is displayed. These manipulations may include changing the cut planes through the volume of image data, translating the center of an image to a specific anatomical location, manipulating to a plane with other anatomical landmarks, rotating a planar view around a given axis by a specific angle, or optimizing the changing by changing rendered slice thickness, the projection algorithm, or some other image optimization parameter. The clinician may also enter data such as labeling certain anatomy with annotations, which are also recorded. When the clinician has completed the image data manipulations needed to arrived at the desired diagnostic image, the clinician stops the recording in step 38. The clinician can then save the recorded 3D review manipulations in step 42. Optionally the clinician can replay the recorded actions and edit them in step 46. For instance, the clinician may want to add instructions on locating the reference image or details on the features which should appear in and thus identify the starting reference image. The user may want to add annotations which label specific anatomy in the succession of image planes. The user may want to paste guide images into the protocol which display to the user examples of what should appear in the images of the sequence. The user may want to delete intermediate manipulations so the recorded manipulations will proceed directly from view "A" to view "C" without the intermediate step of finding view "B". When the recorded review protocol has been edited to the clinician's liking, it is saved in step 42.

Figure 4:
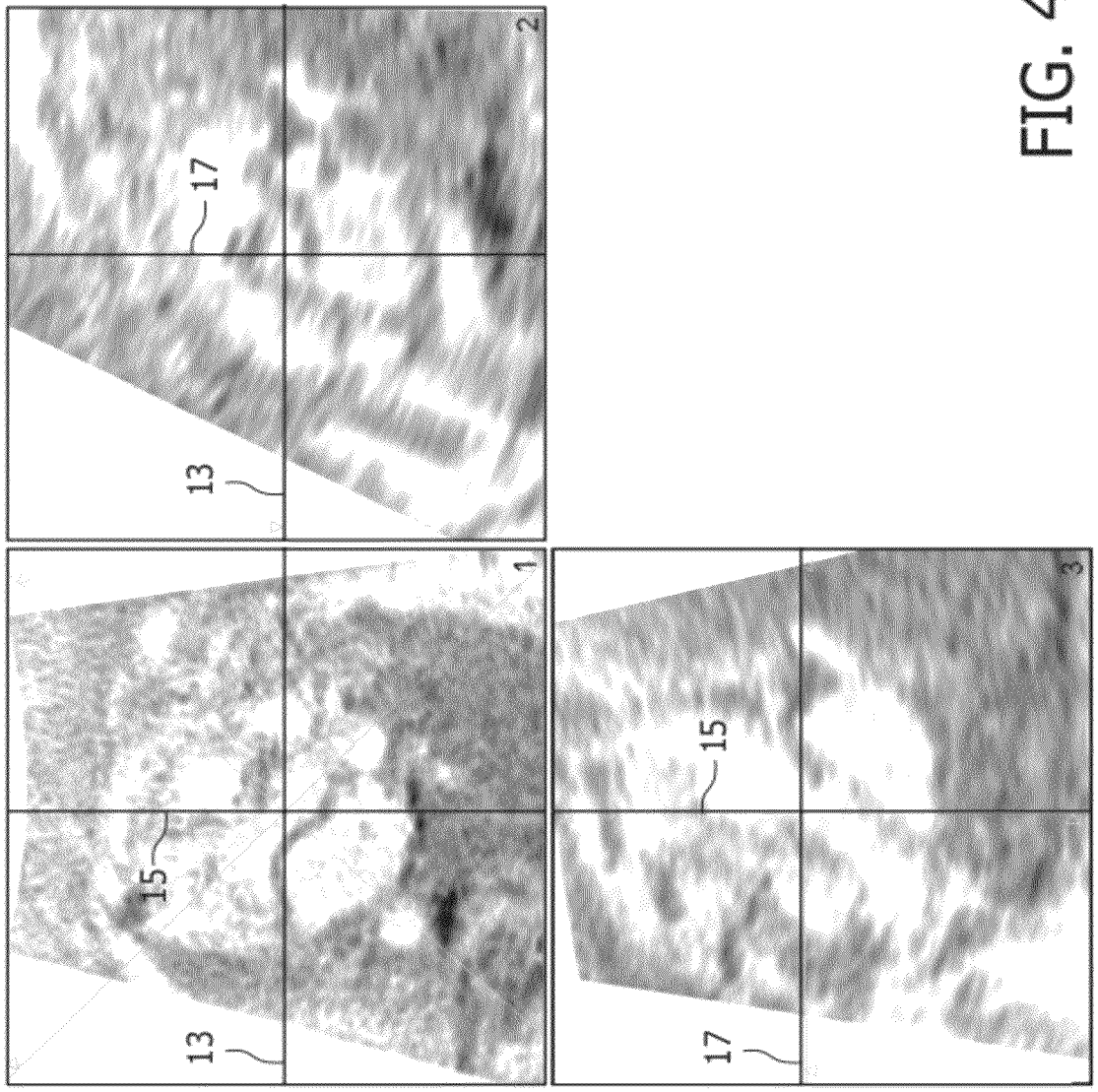
FIGS. 4-7 are a sequence of ultrasound images of 3D image data which explain the development and use of an automated 3D image data review protocol of the present invention.

FIGS. 4, 5, 6, and 7 are a sequence of MPR views of a 3D volume image which illustrate a sequence of recorded image manipulations of a review protocol of the present invention. In this example the clinician has acquired 3D image data encompassing a fetal heart, and desires to examine the left ventricle (LV) and the left ventricular outflow tract (LVOT). The acquired 3D image data is viewed with a 3D MPR viewer that displays three orthogonal MPR planes. When the 3D MPR viewer is initialized, the three orthogonal planes are centered at the center of the 3D image data so that each plane intersects the center of the 3D data and the three planes intersect each other at that point. FIG. 4 illustrates such a display at initialization of the viewer. The three image planes are labeled 1, 2, and 3 in the lower right corner, respectively. The horizontal and vertical lines over each image illustrate the locations of the planes of the other two images. For instance, the horizontal line 13 over image 1 marks the relative location of image plane 3 and the vertical line 15 over image 1 marks the relative location of image plane 2. The horizontal line 13 over image 2 marks the relative location of image plane 3 and the vertical line 17 over image 2 marks the relative location of image plane 1. In a constructed embodiment each image is bordered by a differently colored box and the plane intersection lines are color-coded in correspondence to the colored box of the image plane it demarcates. The user can thereby see from the color coding the relative relationship of the displayed images and their image planes. As FIG. 4 illustrates, at initialization the lines 13, 15, and 17 marking the intersecting planes are all centered on the images.

Figure 5:
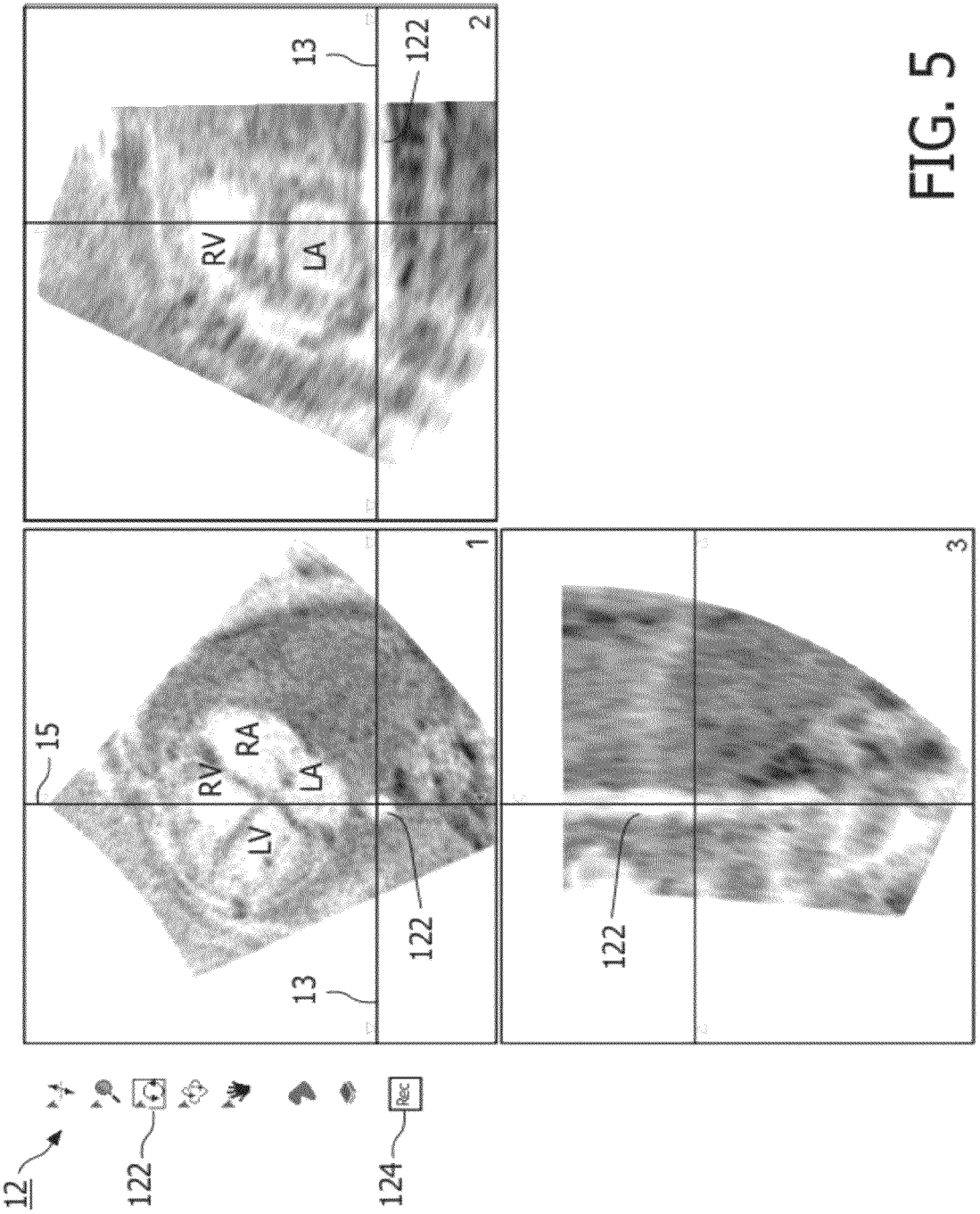

FIG. 5 shows the MPR views after the clinician has located a reference image from which to commence the manipulations necessary to locate the final diagnostic image. The reference image in this example is a cut plane of the 3D volume image which shows a 4-chamber view of the fetal heart and a bisection of the descending aorta. This is done in this example by moving the line 17 for cut plane 1 forward and backward until the desired view appears in plane 1. In a constructed embodiment the clinician does this by pointing at one of the lines labeled 17 and dragging it across the image in which it appears. It may also be necessary to rotate or tilt the volume so that a non-parallel plane can be viewed. This can be done in the illustrated example by clicking on button 122, which changes the cursor to a "tilt" function. The clinician points at one of the images and moves the cursor one way or the other to tilt the inclination of the volume relative to the displayed plane. After these manipulations have been completed, the plane 1 image shows a 4-chamber (LV, RV, LA and RA) view of the fetal heart and also shows a bisection of the descending aorta 12 in the image, as shown in plane 1 of FIG. 5.

Figure 6:
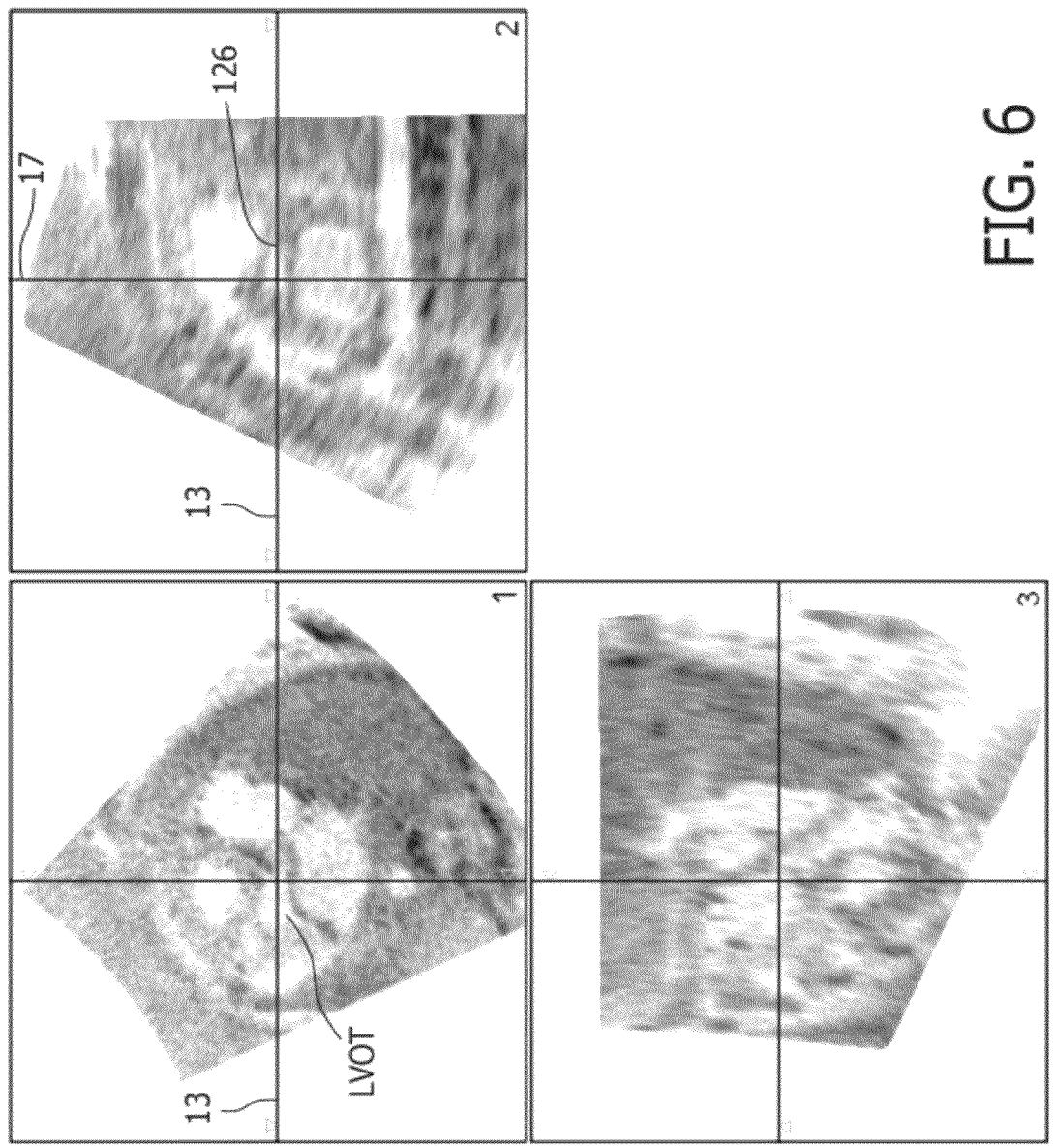
Figure 7:
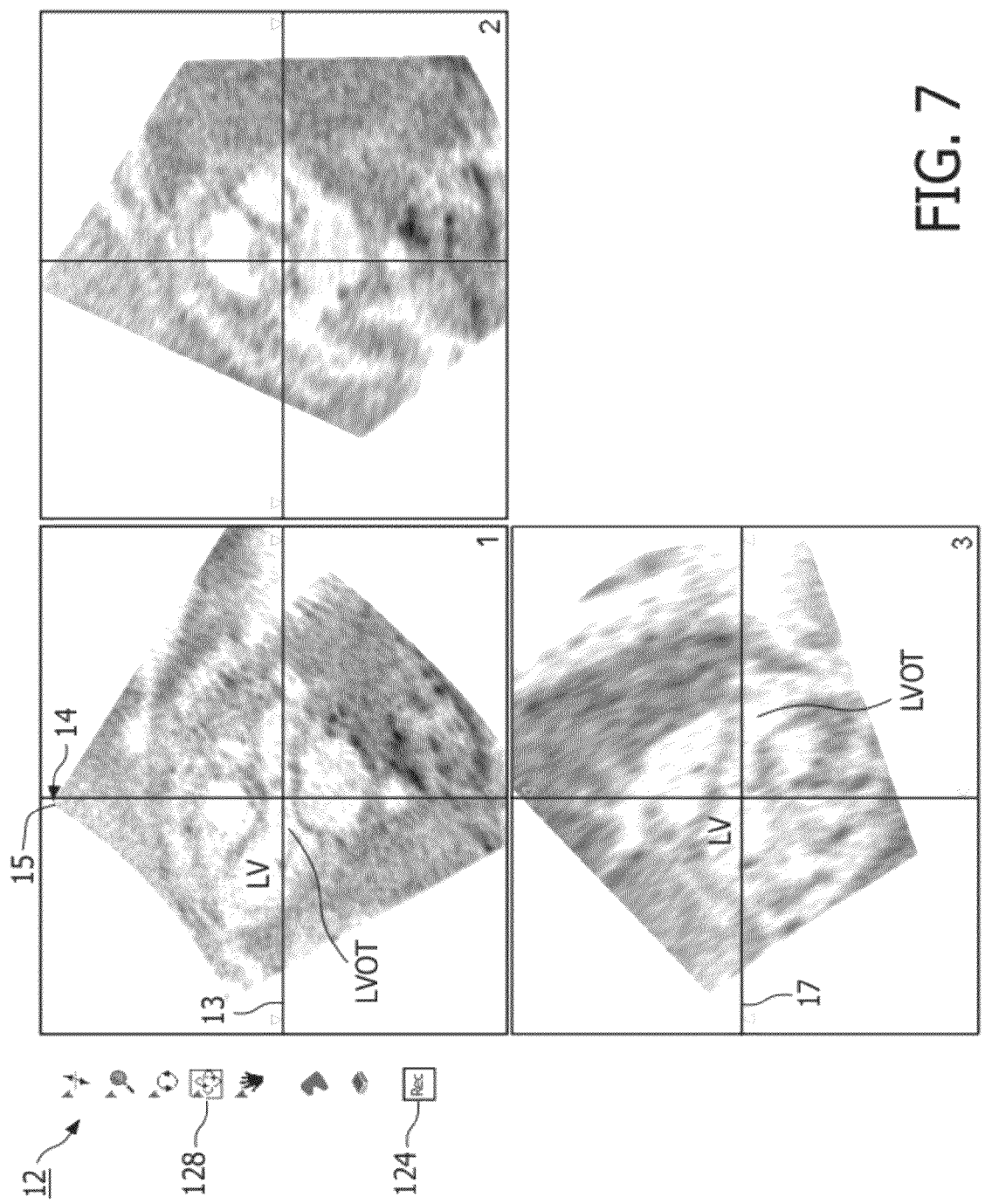

With the reference image presented on the display, the clinician clicks the record button 124 to start recording the manipulations through the 3D image data to arrive at the desired image. The first manipulations are to center the cut plane lines 13 and 15 over plane 1 so that they intersect over the descending aorta. The plane 1 view of FIG. 5 shows the lines 13 and 15 after they have been dragged to intersect the descending aorta 122. When they do, the cut planes of the plane 2 and plane 3 views are seen to longitudinally intersect the descending aorta 122 in each image. In the views now displayed, the next manipulation is to drag the cut plane lines 13 and 17 over plane 2 so that they intersect over the aortic root 126. FIG. 6 is an MPR image display in which lines 13 and 17 have been manipulated in this way. This manipulation causes the cut plane line 13 in plane 1 to intersect the LVOT now revealed in the plane 1 image as shown in FIG. 6. The final manipulation is to rotate the plane 1 image about its y-axis to display a 5-chamber view of the heart. This is accomplished in the constructed embodiment by clicking the "rotate" icon 128 on the left side of the display to cause the cursor to assume a rotate function as shown in FIG. 7. With this function applied, the clinician points at the small arrow 14 at the top of the y-axis, the cut line 15 in plane 1, and moves the cursor. The cut plane of the plane 1 image will then rotate through the 3D image data about the y-axis 15. When the image plane has been rotated the necessary amount the result is the desired 5-chamber view of image plane 1 in FIG. 7, which shows the right atrium (RA), the left atrium (LA), the right ventricle (RV), the LV and the LVOT. With the cut plane line 13 in image plane 1 extending over the LV and LVOT, the LV and LVOT are also now displayed in orthogonal cross-section in the parasternal long axis view of image plane 3. With the desired diagnostic image (s) now shown on the display, the clinician clicks the record button 124 again to stop the recording of the review manipulations. The sequence of manipulations may now be given a name for recall and stored in the ultrasound system disk storage.

Before storing the recorded 3D image review manipulations, the clinician may want to review and edit them. For instance the clinician may want to write instructions for the beginning of the review protocol which instruct a user in obtaining the starting reference image. The clinician may want to annotate anatomical features in the images as shown in FIGS. 5 and 7. The clinician may want the images of this data set to appear to the side as visual guides to a subsequent user of the protocol of what should appear in the images at each stage of the sequence. The clinician may have the protocol compile measurements of spatial relationships between images and image features to develop a statistical database useful for diagnosis. These results can be automatically ported to a system reporting tool for production of a report on the diagnostic exam. The clinician can thus not only edit the results of the current review procedure, but can also store the review protocol with tips, guidance, and further features which make it more user-friendly during subsequent use of the protocol.

When the review protocol is used for a subsequent 3D review procedure by the same clinician or another user, the user will acquire a 3D volumetric image of the fetal heart and call up the review protocol. The user will manipulate the 3D image data to find the reference image plane as instructed at the outset of the protocol. Once the reference image is being viewed, the user will then replay the recorded sequence to quickly move to the desired diagnostic image. The user can replay the complete sequence of manipulations to immediately arrive at a presentation of the desired diagnostic image. Alternatively, the user may replay only one manipulation at a time so that the user can confirm visually that the correct intermediate images are obtained during each step of the automatic review. If one of the intermediate image displays does not appear as anticipated, the user can pause the automated review and make manual adjustments to the displayed images with the manipulation tools described above. Once the desired images(s) is found, the user can resume the protocol to step through or immediately go to the end of the review procedure. This step-wise feature can be useful in a serial study when the anatomy may have changed over time. For instance, a later examination of the fetal heart will generally find that the fetal anatomy has changed by virtue of the intervening development of the fetus. None of the images will be identical to those acquired several weeks or months previously. The clinician may then want to replay the review protocol by stepping the replayed protocol through each manipulation, making manual adjustments needed to account for changes due to fetal development and verifying that each new set of images are the correct ones to arrive at the desired diagnostic image(s)

An automated 3D review protocol of the present invention may find use as a stand-alone feature of an ultrasound system or clinical information system or diagnostic workstation, or as an embedded feature of a more comprehensive protocol. For instance, an acquisition and review protocol could be developed for a comprehensive fetal exam. The acquisition protocol can guide the user through acquisition of 3D image data sets of the head, face, spine, heart, abdomen, and limbs of the fetus, for instance. Following the acquisition of the 3D heart image, the above-described 3D fetal heart review protocol can be embedded in the acquisition protocol to immediately review the acquired 3D fetal heart image data for the desired diagnostic image(s). If the use of the review protocol reveals that the necessary images are not of the desired diagnostic quality, the heart image acquisition step of the acquisition protocol can be repeated to acquire another 3D fetal heart image data set. This procedure can be performed until it is verified that the necessary diagnostic image(s) of the desired diagnostic quality have been obtained. By performing this review and verification during the exam, image acquisition can be repeated until an acceptable 3D image data set has been acquired, obviating the need to call the patient back for another exam.

An automated 3D review protocol of the present invention can be included in the acquiring ultrasound system itself such as the ultrasound system 10 of FIG. 1. The protocol may also be used in diagnostic workstations included in or connected to clinical information systems such as clinical information system 70 of FIG. 1, where 3D image data is reviewed offline following acquisition of the image data by the ultrasound system 10.

What is claimed is:

1. An ultrasonic diagnostic imaging system for reviewing 3D ultrasound image data comprising:
   a 3D ultrasound probe operable to acquire 3D image data of a region of a subject;
   an ultrasound signal path responsive to the acquired 3D image data which produces ultrasound images;

a display coupled to the ultrasound signal path which displays the ultrasound images; and an image review processing unit responsive to a 3D image data set and operable to:
1) locate a reference image in the 3D image data set;
2) manipulate the 3D image data set from a view of the reference image to arrive at a desired diagnostic image;
3) record the manipulations of the 3D image data set; and
4) replay the recorded manipulations from a view of a reference image to arrive at a desired diagnostic image.

2. The ultrasonic diagnostic imaging system of claim 1, wherein the display is operable to display images of three different image planes of a 3D image data set,
wherein the display is used to display images for the image review processing unit.

3. The ultrasonic diagnostic imaging system of claim 1, wherein 4) further comprises replaying the recorded manipulations in a continuous sequence of steps from a view of the reference image to the desired diagnostic image.

4. The ultrasonic diagnostic imaging system of claim 1, wherein 4) further comprises replaying the recorded manipulations in a step-wise sequence of steps from a view of the reference image to the desired diagnostic image.

5. The ultrasonic diagnostic imaging system of claim 4, wherein 4) further comprises manually manipulating the 3D image data set at one or more of the steps of the sequence of steps.

6. An ultrasonic diagnostic imaging system for reviewing 3D ultrasound image data comprising:

a 3D ultrasound probe operable to acquire 3D image data of a region of a subject;

an ultrasound signal path responsive to the acquired 3D image data which produces ultrasound images;

a display coupled to the ultrasound signal path which displays the ultrasound images; and an image review processing unit responsive to a 3D image data set and operable to:
1) locate a reference image in the 3D image data set;
2) manipulate the 3D image data set from a view of the reference image to arrive at a desired diagnostic image;
3) record the manipulations of the 3D image data set; and
4) replay the recorded manipulations from a view of a reference image to arrive at a desired diagnostic image, wherein the display is operable to display images of three different image planes of a 3D image data set, wherein the display is used to display images for the image review processing unit, and wherein 2) includes one or more of the manipulations of changing the plane of an image, translating the center of interest of an image plane to a different anatomical location, rotating an image plane about an axis, and translating an image plane by a certain distance.

7. In an ultrasonic diagnostic imaging system, a method for recording and replaying a review protocol for 3D ultrasonic image data comprising:

acquiring a 3D image data set of a given anatomy;
identifying a reference image of the 3D image data set;
starting a recording of image view manipulations;
manipulating views of images of the 3D image data set starting from a view of the reference image and ending with a desired ending image view;
stopping the recording;
replaying the recording with a 3D image data set, comprising:
acquiring a second 3D image data set of the same type of anatomy;
identifying a reference image of the second 3D image data set; and
replaying the recording to manipulate views of images of the second 3D image data set and ending with a desired ending image view.

8. The method of claim 7, wherein replaying the recording further comprises replaying the recording in a step-wise fashion that pauses after a manipulation.

9. The method of claim 7, wherein replaying the recording further comprises replaying the recording in a continuous fashion from the view of a reference image to a desired ending image view.

10. The method of claim 7, further comprising reviewing and editing the recording.

11. The method of claim 10, wherein editing further comprises at least one of simplifying the steps of manipulation, annotating an image, producing instructions for the review protocol, or including a guide image with the review protocol.

* * * * *